United States Patent [19]

Patoiseau et al.

[11] Patent Number: 5,591,743
[45] Date of Patent: Jan. 7, 1997

[54] 3,5-DIOXO-(2H,4H)-1,2,4-TRIAZINE DERIVATIVES AS 5HT$_{1A}$ LIGANDS

[75] Inventors: Jean-Francois Patoiseau, Castres; Francoise Couret, Corransac; Christian Faure, Toulouse; Elisabeth Dupont-Passelaigue, Castres; Wouter Koek, Viviers-les-Montagnes, all of France

[73] Assignee: Pierre Fabre Medicament, Castres, France

[21] Appl. No.: 578,522
[22] PCT Filed: Jun. 27, 1994
[86] PCT No.: PCT/FR94/00772
  § 371 Date: Mar. 26, 1996
  § 102(e) Date: Mar. 26, 1996
[87] PCT Pub. No.: WO95/01965
  PCT Pub. Date: Jan. 19, 1995

[30] Foreign Application Priority Data

Jul. 6, 1993 [FR] France .................. 93 08259

[51] Int. Cl.⁶ .................. C07D 253/075; A01N 43/707
[52] U.S. Cl. .................. 514/242; 544/182
[58] Field of Search .................. 544/182; 514/242

[56] References Cited

U.S. PATENT DOCUMENTS

| | | | |
|---|---|---|---|
| 4,931,444 | 6/1990 | Van Wauve et al. | 514/252 |
| 4,985,427 | 1/1991 | Waterhouse et al. | 514/242 |
| 5,023,255 | 6/1991 | Ellis et al. | 514/242 |
| 5,424,310 | 6/1995 | Fukami et al. | 514/242 |

FOREIGN PATENT DOCUMENTS

| | | |
|---|---|---|
| 0478954 | 4/1992 | European Pat. Off. |
| 0512755 | 11/1992 | European Pat. Off. |
| 0527081 | 2/1993 | European Pat. Off. |
| 0559285 | 9/1993 | European Pat. Off. |
| WO92/06082 | 4/1992 | WIPO |

OTHER PUBLICATIONS

Lazurkevich et al., Growth activity of 6–substituted azauracils, Fiziol. Biokhim. Kul't. Rast. (1985), 17(1), pp. 48–54 1985.

Tzeng et al., 4–Azapteridines. 2[1]. Spectral, Chromatographic, and X–Ray Crystallographic Studies concerning the Mode of Covalent Addition to the Pyrazino[2,3–e]–as–triazine Ring system, J. Heterocyclic Chem., 23, (1986), pp. 33–42 1986.

Journal of Medicinal Chemistry, 35, No. 13, pp. 2369–2374 (1992); Jerzy L. Mokrosz et al., "Structure–activity relationship studies of central nervous system agents. 5. Effect of . . . ".

Primary Examiner—Mukund J. Shah
Assistant Examiner—Deepak R. Rao
Attorney, Agent, or Firm—The Firm of Gordon W. Hueschen

[57] ABSTRACT

A 3,5-dioxo-(2H,4H)-1,2,4-triazine compounds of formula I

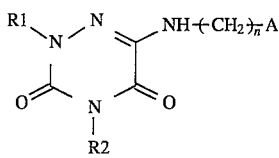

in which:

$R_1$ and $R_2$, which are identical or different, represent hydrogen or $C_1$–$C_6$ alkyl, n is 2 to 6, inclusive, A represents aryl piperazino II

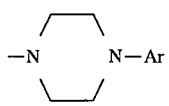

the Ar grouping representing phenyl, naphthyl, pyrimidyl, or pyridyl, unsubstituted or substituted by $C_1$–$C_3$ alkyl, $C_1$–$C_3$ alkoxy, hydroxy, trifluoromethyl, or halogen, or III benzodioxanyl-methyl-amino or pyridodioxanyl-methyl-amino

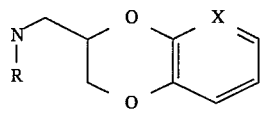

in which R represents hydrogen or $C_1$–$C_3$ alkyl and X represents a nitrogen or carbon atom, therapeutically-acceptable salts and enantiomers thereof, pharmaceutical compositions thereof, and method for treatment of diseases requiring a 5HT$_{1A}$ receptor agonist therewith.

12 Claims, No Drawings

3,5-DIOXO-(2H,4H)-1,2,4-TRIAZINE DERIVATIVES AS 5HT$_{1A}$ LIGANDS

The present invention relates to new derivatives of 3,5-dioxo-6 amino-(2H,4H)-1,2,4-triazine, their preparation and their therapeutic use.

In the search for new anxiolytic drugs having a non-benzodiazepine profile, the discovery and development of Buspirone has resulted in a large amount of work. In fact, during recent years, numerous compounds having an affinity for 5HT1A receptors have been claimed for their anxiolytic and/or antihypertensive activity (J. Peergaard, et al., Current opinion in therapeutic Patents, January 1993, 101–128).

The compounds of the present invention are characterized by their original structure, their powerful affinity for the 5HT1A receptor, and their pharmacological profile.

The compounds of the invention correspond to general formula I

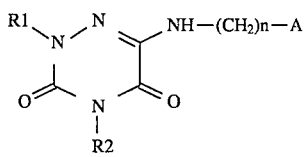

in which:
R$_1$ and R$_2$, which are identical or different, represent hydrogen or a C$_1$–C$_6$ alkyl radical,
n may assume the integral values of 2 to 6,
A represents a grouping such as
aryl piperazino II

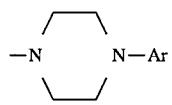

the Ar grouping in its turn representing an aromatic structure such as phenyl, naphthyl, pyrimidyl or pyridyl, possibly substituted by one or more groupings such as C$_1$–C$_3$ alkyl, C$_1$–C$_3$ alkoxy, hydroxy, trifluoromethyl or halogen.
benzodioxanyl methyl amino or pyridodioxanylmethyl amino III

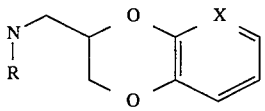

in which R represents hydrogen or a C$_1$–C$_3$ alkyl grouping and X represents a nitrogen or carbon atom.

Furthermore, the invention covers the salts of the compounds of general formula I with pharmaceutically acceptable acids in the case of compounds of sufficient basicity, as well as the various enantiomers for the compounds having an asymmetric carbon.

The compounds of the invention can be obtained by a chemical process characterized by condensing a compound of general formula IV.

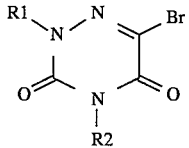

with a compound of general formula V,

the radicals R$_1$, R$_2$, n, and A having the same meaning in IV and V as in general formula I.

The compounds of general formula IV are themselves obtained in accordance with the invention as described below:

a) When R$_1$=R$_2$=H, by bromination of 3,5-dioxo-(2H,4H)-1,2,4-triazine by bromine in aqueous medium.

b) When R$_1$ =R$_2$ =alkyl, by alkylation of 3,5-dioxo(2H,4H)-1,2,4-triazine in the presence of sodium hydride in DMF by an alkyl halide, followed by bromination by the same method as a) above. For the alkylation it is necessary, as intermediate step, to isolate the mixture of monoalkyl compounds formed and to carry out the alkylation operation again under the same conditions in order to have a complete reaction.

c) When R$_1$=H and R$_2$=alkyl from 3,5-dioxo-(2H,4H)-1,2,4-triazine by:
1—acetylation in 2 position by treatment with acetic anhydride or acetyl chloride
2—alkylation of the 4 position by an alkyl halide R$_2$X in the presence of NaH in DMF, X representing Cl, Br or I
3—desacetylation in acid medium such as p-toluene sulfonic acid in ethanol
4—bromination by the method previously described.

d) When R$_1 \neq$R$_2$=alkyl, by alkylation of the compound obtained in accordance c/3 by an alkyl halide R$_1$X in the presence of NaH in DMF, X representing Br, Cl or I, followed by bromination as described previously.

e) When R$_1$=alkyl and R$_2$=H, by:
1—synthesis of 3-thiooxo-5-oxo-(2H,4H)-1,2,4-triazine by condensation of glyoxylic acid with the thiosemicarbazide followed by a base treatment
2—methylation by methyl iodide in the presence of NaH in DMF
3—alkylation in 2 position by an alkyl halide R$_1$X in the presence of NaH in DMF, X representing Cl, Br or I
4—treatment in acid medium such as hydrochloric acid
5—bromination by the method previously described.

The preparation of the compounds I for which R$_1$=R$_2$=H can also be advantageously carried out by condensing the amine V with the brominated and acetylated compound VI

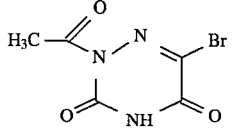

and then treating the resultant derivative in acid medium such as hydrochloric acid or p-toluenesulfonic acid.

The compound VI is in its turn obtained by the acetylation with acetic anhydride or acetyl chloride of 6-bromo-3,5-dioxo-(2H,4H)-1,2,4-triazine.

The compounds V are commercial amines or can be obtained in conventional manner such as generation of the primary amine from the intermediate phthalimide.

The following examples illustrate the invention without limiting its scope.

The elementary analyses and the IR and NMR spectra confirm the structures of the compounds obtained by the invention.

EXAMPLE 1:

2,4-dimethyl-3,5-dioxo- (2H, 4H)-6-(4-(4-(3-trifluoromethylphenyl)piperazino)-butylamino)-1,2,4-triazine 1.

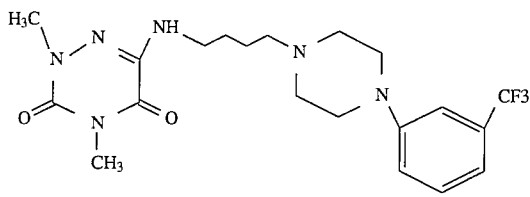

a) 2,4-dimethyl-3,5-dioxo(2H,4H)-1,2,4-triazine 1a.

To a 60% suspension of sodium hydride in paraffin oil (8.8 g; 0.22 mol) in DMF (100 ml), a solution of 3,5-dioxo-(2H, 4H)-1,2,4-triazine (25 g; 0.22 mol) in DMF (350 ml) is added drop by drop. After stirring for 30 minutes at room temperature, methyl iodide (27.4 ml) is added and it is kept, without agitation, overnight. After concentration to dryness under vacuum, the residue is taken up in DMF (300 ml) and 60% sodium hydride is added (8.8 g; 0.22 mol). After agitation for 4 hours, the methyl iodide is added (27.4 ml) and agitation is effected overnight at room temperature. The reaction mixture is concentrated to dryness under vacuum, taken up in a saturated aqueous solution of NaCl (100 ml) and extracted with ethyl acetate (5×200 ml). The combined organic phases are dried ($Na_2SO_4$) and concentrated to dryness under vacuum. After crystallization, washing with water, and drying under vacuum, compound 1a is obtained (16.43 g).

F=64° C. TLC: Silica gel 60 F 254 Merck $CH_2Cl_2$/ethyl acetate 70:30 RF: 0.53 b) 6-bromo-2,4-dimethyl-3,5-dioxo-(2H,4H)-1,2,4-triazine 1b.

Compound 1a (13.3 g) is treated in water (100 ml) with bromine (18 ml) for 12 hours at 60° C. After evaporation under vacuum, the reaction mixture is extracted with ethyl acetate (2×100 ml). The organic phases, combined, are dried ($MgSO_4$) and evaporated to dryness under vacuum. After recrystallization in ethyl ether, the compound 1b (7.8 g) is obtained which is used as is in the following step.

c) 2,4-dimethyl-3,5-dioxo[2H, 4H]-6-[4-(4-(3-trifluoromethylphenyl)piperazino)-butylamino]-1,2,4-triazine 1.

Compound 1b (1 g) and 4-(4-(3-trifluoromethylphenyl)piperazino)butylamine (1.4 g) are heated for 3 hours under reflux of n-butanol (30 ml) in the presence of triethylamine (2 ml). This reaction mixture is concentrated under vacuum, taken up to 1N sodium hydroxide, and extracted with dichloromethane (2×100 ml). These dried organic phases ($Na_2SO_4$) are concentrated in vacuum and chromatographed on silica gel (87 g). The 80:15:5 isopropyl-ether/dioxan/triethylamine mixture elutes the compound 1, which is purified, after evaporation of the solvent, by recrystallization in isopropyl ether.

MP=87° C. TLC: Silica gel 60 F 254 Merck Isopropyl-ether/dioxan/triethylamine 80:15:5 Rf=0.3

EXAMPLE 2

2,4-dimethyl-3,5-dioxo-(2H,4H)-6-(4(4-(3-chlorophenyl) piperazino)butylamino)-1,2,4-triazine 2.

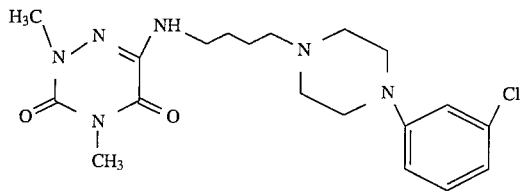

This compound is prepared by the process described in Example 1, using 4-(4-(3-chlorophenyl) piperazino) butylamine in step c).

MP=122° C. TLC: Silica gel 60 F 254 Merck Isopropyl-ether/dioxan/triethylamine 80:15:5 Rf=0.3

EXAMPLE 3

2,4-dimethyl-3,5-dioxo-(2H,4H)-6-(4-(4-(2-methoxyphenyl) piperazino)butylamino)-1,2,4-triazine 3.

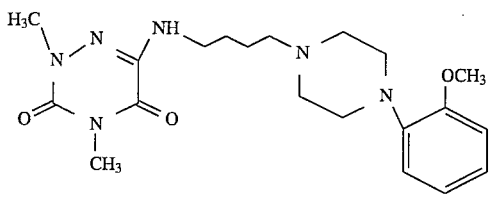

This compound is prepared by the process described in Example 1, using the 4-(4- (2-methoxyphenyl) piperazino) butylamine in step c).

MP=122° C. TLC: Silica gel 60 F 254 Merck Isopropyl-ether/dioxan/triethylamine 80:15:5 Rf=0.3

EXAMPLE 4

2,4-dimethyl-3,5-dioxo- (2H, 4H)-6-(4-(4-(4-chlorophenyl) piperazino) butylamino) -1,2,4-triazine 4.

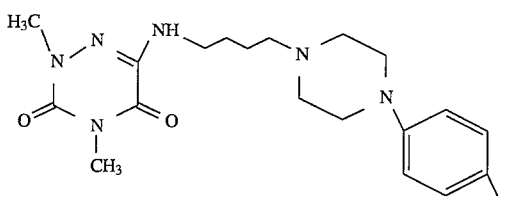

This compound is prepared by the process described in Example 1, using 4-(4-(4-chlorophenylpiperazino) butylamine in step c).

MP=102° C. TLC: Silica gel 60 F 254 Merck Isopropyl-ether/dioxan/triethylamine 80:15:5 Rf=0.35

EXAMPLE 5

2,4-dimethyl-3,5-dioxo- (2H, 4H)-6-(4-(4-(2-pyrimidyl) piperazino)butylamino)-1,2,4-triazine.

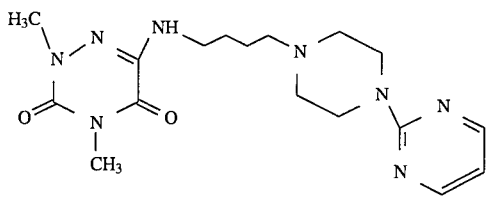

This compound is prepared by the process described in Example 1, using 4-(4-(2-pyrimidyl) piperazino) butylamine in step c).

MP=120° C. TLC: Silica gel 60 F 254 Merck Isopropyl= ether/dioxan/triethylamine 85:10:5 Rf=0.2

EXAMPLE 6

2,4-dimethyl-3,5-dioxo-(2H,4H)-6-(3-(4-(3-trifluoromethylphenyl)piperazino)propylamino)-1,2,4-triazine 6.

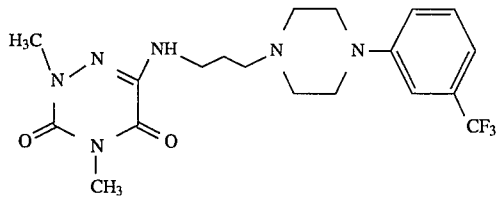

This compound is prepared by the process described in Example 1, using the 3-(4-(3-trifluoromethylphenyl)piperazino)propylamine in step c).

MP=109° C. TLC: Silica gel 60 F 254 Merck Isopropyl-ether/dioxan/triethylamine 85:10:5 Rf=0.3

EXAMPLE 7

2,4-dimethyl-3,5-dioxo (2H, 4H)-6-(2-(4-(3-trifluoromethylphenyl)piperazino)-ethylamino)-1,2,4-triazine 7.

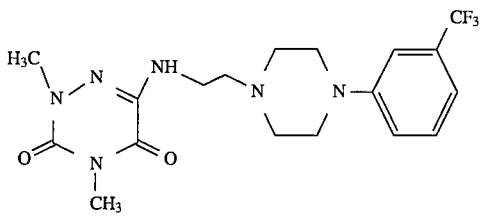

This compound is prepared by the process described in Example 1, using 2-(4-(3-trifluoromethylphenyl)piperazino)ethylamine in step c).

MP=90° C. TLC: Silica gel 60 F 254 Merck Isopropyl-ether/dioxan/triethylamine 85:10:5 Rf=0.33

EXAMPLE 8

2,4-dimethyl-3,5-dioxo-(2H, 4H)-6-(3-(4-(3-trifluoromethylphenyl)piperazino)-propylamino)-1,2,4-triazine 8.

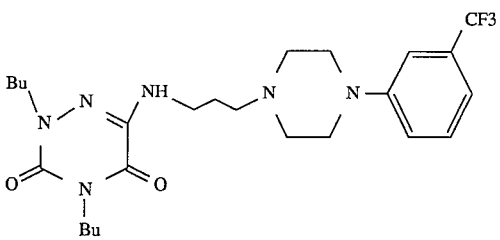

This compound is prepared by the process described in Example 1, using butyl bromide in step a) and 3-(4-(3-trifluoromethylphenyl)piperazino)propylamine in step c).

MP=66° C. TLC: Silica gel 60 F 254 Merck Isopropyl= ether/dioxan/triethylamine 85:15:5 Rf=0.48

EXAMPLE 9

2,4-dimethyl-3,5-dioxo-(2H,4H)-6-(4-(1,4-benzodioxan-2 ylmethylamino)butylamino)-1,2,4-triazine 9.

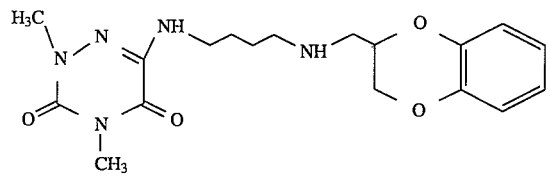

This compound is prepared by the process described in Example 1, using 4-(1,4-benzodioxan-2-ylmethylamino) butylamine in step c).

MP=214° C. (hydrochloride) TLC: Silica gel 60 F 254 Merck Isopropyl-ether/dioxan/triethylamine 80:15:5 Rf=0.2

EXAMPLE 10

2,4-dimethyl-3,5-dioxo-(2H, 4H)-6-(3-(1,4-benzodioxan-2 ylmethylamino)propylamino)-1,2,4-triazine 10.

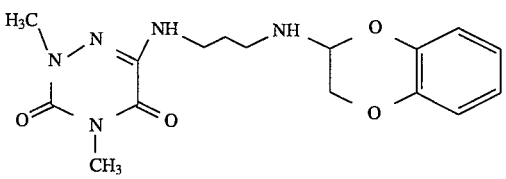

This compound is prepared by the process described in Example 1, using 3-(1,4-benzodioxan-2-ylmethylamino)-propylamine in step c).

MP=120° C. TLC: Silica gel 60 F 254 Merck Chloroform/methanol 90:10 Rf=0.42

EXAMPLE 11

4-butyl-3,5-dioxo-(2H, 4H)-6-(4-(4-(3-trifluoromethylphenyl)piperazino)-butylamino)-1,2,4-triazine 11.

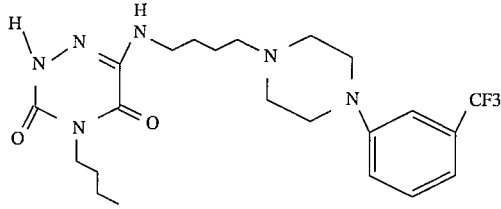

a) 2-acetyl-3,5-dioxo-(2H,4H)-1,2,4-triazine 11a.

3,5-dioxo-(2H,4H)-1,2,4-triazine (48.88 g) is heated under reflux of acetic anhydride (300 ml) for 90 minutes. After cooling and concentration to dryness under vacuum, the residue is taken up in toluene (300 ml) and cooled at 0° C. for 2 hours. The white precipitate which forms is filtered off, centrifuged, and dried under vacuum at 70° C. so as to give the compound 11a (57.6 g).

MP=150° C. TLC: Silica gel 60 F 254 Merck $CH_2Cl_2$/MeOH: 85:15 Rf=0.61 b) 4-butyl-3,5-dioxo-(2H,4H)-1,2,4-triazine 11b.

To a 50% sodium hydride suspension (4.8 g) in DMF (100 ml), compound 11a (15.5 g) dissolved in DMF (200 ml) is added drop by drop, maintaining the temperature at room temperature. After agitation for 2 hours, bromobutane (20 g) is added and the agitation continued for 12 hours. The reaction mixture is concentrated to dryness under vacuum at 60° C., taken up in water, and then extracted with methylene chloride. After concentration to dryness under vacuum, the oil is taken up in ethanol (100 ml), whereupon p-toluene-sulfonic acid (2 g) is added. After heating under reflux for 2 hours and leaving at room temperature for 12 hours, the reaction mixture is filtered. The precipitate is washed with an aqueous solution of sodium bicarbonate and water, and then dried in an oven under vacuum in order to give the compound 11b (8.7 g).

MP=135° C. TLC: Silica gel 60 F 254 Merck $CHCl_3$/MeOH: 9:1 Rf=0.35 c) 4-butyl-3,5-dioxo-(2H,4H)-6-(4-(4-(3-trifluoromethyl-phenyl)piperazino)butylamino)-1,2,4-triazine 11

Compound 11b is treated in the same way as that described in Example 1b and 1c in order to obtain compound 11.

MP=140° C. (hydrochloride) TLC: Silica gel 60 F 254 Merck Isopropyl-ether/dioxan/triethylamine 80:15:5 Rf=0.45

EXAMPLE 12:

4-butyl-3,5-dioxo-(2H, 4H)-6-(3-(4-(3-trifluoromethylphenyl)piperazino)-propylamino)-1,2,4-triazine 12.

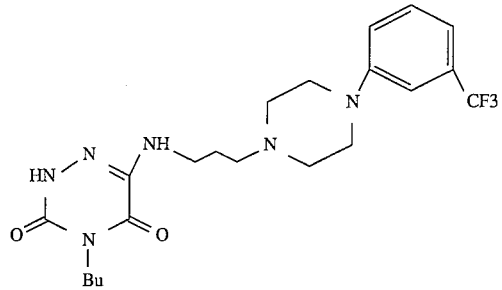

This compound is prepared by the process described in Example 11 using 3-(4-(3-trifluoromethyl-phenyl)piperazino) propylamine in the final step.

MP=154° C. TLC: Silica gel 60 F 254 Merck Isopropyl-ether/dioxan/triethylamine 80:15:5 Rf=0.40

EXAMPLE 13:

4-butyl-3,5-dioxo-(2H, 4H)-6-(2-(4-(3-trifluoromethylphenyl)piperazino)-ethylamino)-1,2,4-triazine 13.

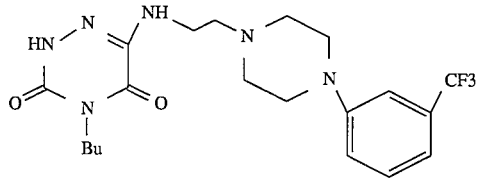

This compound is prepared by the process described in Example 11, using 2-(4-(3-trifluoromethylphenyl)piperazino)ethylamine in the final step.

MP=149° C. TLC: Silica gel 60 F 254 Merck Isopropyl-ether/dioxan/triethylamine 80:15:5 Rf=0.35

EXAMPLE 14:

2-methyl-3,5-dioxo-(2H,4H)-6-(4-(4-(3-trifluoromethylphenyl)piperazino)butylamino)-1,2,4-triazine 14.

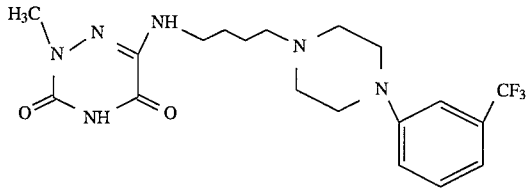

a) 3-thioxo-5-oxo-(2H,4H)-1,2,4-triazine 14a.

To a 50% solution of glyoxylic acid (148 g; 110 ml) in water (1 liter), there is added a solution of thiosemicarbazide (91.1 g) in water (1 liter) at 70° C. After agitation for 1 hour, the mixture is set aside for 12 hours at 0° C. The precipitate formed is filtered, centrifuged and dried under vacuum in the presence of $P_2O_5$ at 70° C.

The compound thus obtained (112 g) is taken up by 1N caustic soda (1500 ml) and brought to reflux for 3 hours. After cooling to room temperature, acetic acid (91 ml) is added drop by drop and the mixture is set aside overnight. The precipitate formed is filtered off, centrifuged and dried under vacuum at 80° C. in the presence of $P_2O_5$ in order to give the compound 14a (62 g).

MP=260° C.

b) 3-methylthio-5-oxo-(2H)-1,2,4-triazine 14b.

Compound 14a (62 g) dissolved in 2N sodium hydroxide (480 ml) is treated with a solution of methyl iodide (30 ml). After 2 hours at room temperature with agitation, the acetic acid (36 ml) is added drop by drop and the mixture set aside overnight at 0° C. The precipitate formed is filtered, centrifuged, and dried under vacuum at 60° C. in the presence of $P_2O_5$ in order to obtain the compound 14b (56.4 g).

MP=215° C.

c) 2-methyl-3,5-dioxo-(2H,4H)-1,2,4-triazine 14c.

Compound 14b (14.3 g) dissolved in DMF (140 ml) is added to a 60% NaH suspension (4.2 g) in DMF (40 ml).

After agitation for 2 hours at ordinary temperature, methyl iodide (7.5 ml) is added and it is agitated for 12 hours more. After concentration under vacuum, the residue is taken up in water (20 ml) and extracted with methylene chloride (2×50 ml). The organic phases, dried ($Na_2SO_4$), are concentrated to dryness under vacuum. The brown oil thus obtained (14.2 g) is treated with 2N hydrochloric acid (80 ml) for 30 minutes at 100° C. After cooling, the reaction mixture is extracted with methylene chloride (2×50 ml). The organic phases are dried ($Na_2SO_4$) and concentrated under vacuum. The residue is taken up in hot ethyl ether (100 ml), treated with activated charcoal and concentrated to dryness under vacuum. By recrystallization from toluene, compound 14c is obtained after drying at 60° C. under vacuum (2.6 g).

MP=118° C.

d) 2-methyl-3,5-dioxo-(2H, 4H)-6-(4-(4-(3-trifluoromethylphenyl)piperazino)-butylamino)-1,2,4-triazine 14.

The compound 14c is treated in a manner identical to that described in Example 1b and 1c to obtain the compound 14.

TLC: Silica gel 60 F 254 Merck Isopropyl-ether/dioxan/triethylamine 80:15:5 Rf=0.40

EXAMPLE 15:

3,5-dioxo-(2H,4H)-6-(4-(4-(3-trifluoromethylphenyl)-piperazino)butylamino)-1,2,4-triazine 15.

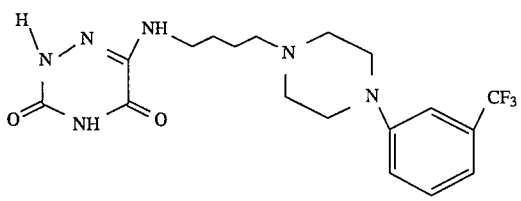

a) 2-acetyl-6-bromo-3,5-dioxo-(2H,4H)-1,2,4-triazine 15a.

The 6-bromo-3,5-dioxo-(2H,4H)-1,2,4-triazine (5 g) obtained from the 3,5-dioxo-(2H,4H)-1,2,4-triazine in accordance with the technique described in example 1b is treated with acetic anhydride (50 ml) for 7 hours under reflux. After concentration to dryness under vacuum and taking up in ethyl ether, the precipitate is filtered, centrifuged, and dried under vacuum at 50° C. to give compound 15a (4.6 g).

b) 3,5-dioxo-(2H,4H)-6-(4-(4-(3-trifluoromethylphenyl)-piperazino)butylamino)-1,2,4-triazine 15.

The compound 15a (2.44 g) in solution in butanol (15 ml) is treated with 4-(4-(3-trifluoromethylphenyl)piper-azino)butylamine (2.88 g) in the presence of triethylamine (1.5 ml) under reflux for 8 hours. After concentration to dryness under vacuum and taking up in ethanol (50 ml), p-toluenesulfonic acid is added (1.5 g), refluxing for 4 hours. The reaction mixture is concentrated to dryness under vacuum, taken up in water (100 ml) and extracted with ethyl acetate (3×200 ml). The dried organic phases ($Na_2SO_4$) are concentrated and chromatographed over silica. After concentration to dryness under vacuum, the 90:10 CH2Cl2-MeOH mixture gives the derivative 15 (1.26 g).

MP=94° C. TLC: Silica gel 60 F 254 Merck $CH_2Cl_2$/MeOH/$NH_4OH$ 90:9:1 Rf=0.46

The compounds of the invention were subjected to pharmacological tests which showed their suitability as active substances in therapy.

Thus, they were the object of a study relating to their affinity for serotoninergic receptors such as $5-HT_{1A}$.

The study of the bonding to the receptor $5-HT_{1A}$ is carried out in the manner described by Sleight and Peroutka (Naunyn-Schmiedebergs Arch. Pharmacol. 343:106–116, 1991). For these experiments, rat cerebral cortices are used. The brain is dissected and the cortex is homogenized in 20 volumes of Tris-HCl buffer (50 mM, pH 7.4 at 25° C.) kept at 4° C. The homogenate is centrifuged at 39000 g for 10 minutes, the final product is suspended in the same volume of buffer and centrifuged again. After being again placed in suspension under the same conditions, the homogenate is incubated for 10 minutes at 37° C. and then centrifuged again. The final product is suspended in 80 volumes of reaction buffer containing pargyline ($10^{-5}$M), $CaCl_2$ (4 mM) and ascorbic acid (0.1%) in Tris-HCl (50 mM, pH 7.4 at 25° C.). The final concentration of tissue in the incubation medium is 10 mg/tube.

In the saturation experiments, the reaction tubes contain 0.1 ml of different concentrations of [$^3$H]8—OH—DPAT (between 0.06 and 8 nM), 0.1 ml of reaction buffer 5-HT ($10^{-5}$M, in order to determine the non-specific bond) and 0.8 ml of tissue.

The displacement experiments are carried out in the manner described by Sleight and Peroutka (Naunyn-Schmiedebergs Arch. Pharmacol. 343:106–116, 1991). All the dilutions of products to be studied are prepared in the reaction buffer. The reaction tubes contain 0.1 ml of [$^3$H]8-OH-DPAT (0.2 nM), 0.1 ml of product to be tested 6–7 concentrations (successive dilutions to ⅒) and 0.8 ml of tissue. If the presumed affinity of the products is in the nanomolar range, the smallest concentration tested is 10⁻¹¹M, and if the product has a low presumed affinity, the highest concentration tested is 10⁻⁴M. The reaction tubes are incubated at 23° C. for 30 minutes and then rapidly filtered under vacuum on Whatman GF/B filters; the tubes are rinsed with 2×5 ml of Tris-HCl buffer (50 mM, pH 7.4 at 25° C.). The radioactivity collected on the filter is analyzed in liquid scintillation by adding 4 ml of scintillating liquid (Emulsifier Safe, Packard). All the experiments are carried out in triplicate and repeated at least 3 times.

The dissociation constant ($K_D$) and the maximum number of bond sites ($B_{max}$) for the radioligand are estimated on the basis of the saturation experiments using the non-linear regression program EBDA/LIGAND (Biosoft) (Munson and Rodbard: Anal. Biochem. 107:220–239, 1980). The affinity constants (Ki) of the reference products are estimated on the basis of the displacement experiments using the EBDA/LIGAND non-linear regression program. This method permits the value of Hill's coefficient to be not different from unity. The data of the displacement experiments are analyzed with the one-site and two-site models respectively and the calculated F makes it possible to determine whether the two-site model is more representative of the data obtained than the one-site model. The values of pKi are given in the form of the average ±SEM of 3 to 5 experiments.

Table 2 shows, by way of example, the pKi 5-HT$_{1A}$ for certain derivatives of the invention, with respect to Buspirone, which is used in clinical practice.

TABLE 2

| Affinity for the receptor 5-HT$_{1A}$. | |
|---|---|
| Compound No. | pKi |
| 1 | 9.50 |
| 2 | 9.40 |
| 3 | 9.21 |
| 6 | 7.79 |
| 9 | 8.57 |
| 10 | 8.42 |
| 11 | 7.90 |
| Buspirone | 7.95 |

The results of the tests show that the compounds of general formula I have a high affinity for the serotoninergic receptors of 5-HT$_{1A}$ type.

The central activity of the compounds of the invention was evaluated by their capacity to provoke the 5-HT syndrome which is characterized by an alternate flexure and extension of the forepaws (reciprocal fore-paw treading: FPT), the retraction of the lower lip (lower-lip retraction: LLR) and by a posture in which the ventral surface of the animal is in contact with the floor of the cage, with the hind paws extended (flat body posture: FBP).

The experiments of the evaluation of the 5-HT syndrome are carried out on the male rat (Sprague-Dawley) by the method described by F. C. Colpaert et al. (Drug. Dev. Res. 26:21–48, 1992).

Table 3 shows, by way of example, the active doses (ED$_{50}$) for certain derivatives of the invention as compared with a reference product, Buspirone.

TABLE 3

| 5-HT Syndrome | | | |
|---|---|---|---|
| | ED$_{50}$: mg/kg, i.p. | | |
| Compound No. | FBP | LLR | FPT |
| 1 | 0.31 | 0.31 | 0.31 |
| 2 | 0.31 | 0.31 | 40 |
| Buspirone | 5.0 | 1.25 | >40 |

The results of the tests show that the compounds of general formula I have, in vitro, a high affinity for the serotoninergic receptors of type 5-HT$_{1A}$. In vivo, they show an agonistic activity at the level of these receptors.

The compounds of the invention can therefore be useful for the treatment of anxiety, depression, disturbances in sleep, for the regulating of food intake, the regulating of gastric secretion, and the treatment of vascular, cardiovascular and cerebrovascular disorders such as hypertension or migraine.

The pharmaceutical preparation containing these active principles can be formulated for administration by oral, rectal or parenteral route, for instance in the form of capsules, tablets, granules, gelules, liquid solutions, drinkable syrups or suspensions, and can contain suitable excipients.

It is also possible to combine other pharmaceutically and therapeutically acceptable active principles with them.

We claim:

1. A 3,5-dioxo-(2H,4H)-1,2,4-triazine compound selected from those of formula I

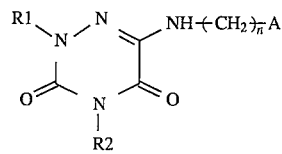

in which:

R$_1$ and R$_2$, which are identical or different, represent hydrogen or C$_1$–C$_6$ alkyl, n is 2 to 6, inclusive, A represents
aryl piperazino

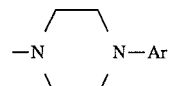

the Ar grouping representing phenyl, naphthyl, pyrimidyl, or pyridyl, unsubstituted or substituted by C$_1$–C$_3$ alkyl, C$_1$–C$_3$ alkoxy, hydroxy, trifluoromethyl, or halogen, or benzodioxanyl-methyl-amino or pyridodioxanyl-methylamino

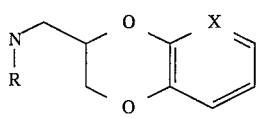

in which R represents hydrogen or C$_1$–C$_3$ alkyl and X represents a nitrogen or carbon atom, and the therapeutically-acceptable organic or inorganic salts of these molecules and the enantiomers of those having an asymmetric carbon.

2. A compound of claim 1, selected from the group consisting of:

2,4-dimethyl-3,5-dioxo-(2H,4H)-6-(4-(4-(3-trifluoromethylphenyl)piperazino)butylamino)-1,2,4-triazine, 2,4-dimethyl-3,5-dioxo-(2H,4H)-6-(4-(4-(3-chlorophenyl) piperazino)butylamino)-1,2,4-triazine, 2,4-dimethyl-3,5-dioxo-(2H,4H)-6-(4-(4-(2-methoxyphenyl) piperazino)butylamino)-1,2,4-triazine, 2,4-dimethyl-3,5-dioxo-(2H,4H)-6-(4-(4-(4-chlorophenyl) piperazino)butylamino)-1,2,4-triazine, 2,4-dimethyl-3,5-dioxo-(2H,4H)-6-(4-(4-(2-pyrimidyl)piperazino)butylamino)-1,2,4-triazine, 2,4-dimethyl-3,5-dioxo-(2H,4H)-6-(3-(4-(3-trifluoromethylphenyl)piperazino)propylamino)-1,2,4-triazine, 2,4-dimethyl-3,5-dioxo-(2H,4H)-6-(2-(4-(3-trifluoromethylphenyl)piperazino)ethylamino)-1,2,4-triazine, 2,4-dibutyl-3,5-dioxo-(2H,4H)-6-(3-(4-(3-trifluoromethylphenyl)piperazino)propylamino)-1,2,4-triazine, 2,4-dimethyl-3,5-dioxo-(2H,4H)-6-(3-(1,4-benzodioxan-2-yl-methylamino)propylamino)-1,2,4-triazine, 4-butyl-3,5-dioxo-(2H,4H)-6-(4-(4-(3-trifluoromethylphenyl) piperazino)butylamino)-1,2,4-triazine,.

4-butyl-3,5-dioxo-(2H,4H)-6-(3-(4-(3-trifluoromethylphenyl) piperazino)propylamino)-1,2,4-triazine, 4-butyl-3,5-dioxo-(2H,4H) -6-(2-(4-(3-trifluoromethylphenyl)piperazino)ethylamino)-1,2,4-triazine, 2-methyl-3,5-dioxo-(2H,4H)-6-(4-(4-(3-trifluoromethylphenyl) piperazino)butylamino)-1,2,4-triazine, and 3,5-dioxo-(2H,4H)-6-(4-(4-(3-trifluoromethylphenyl)piperazino)butylamino)-1,2,4-triazine, and pharmacologically-acceptable salts thereof.

3. A method for the treatment of a disease requiring an agonist of $5HT_{1A}$ receptors, the step of administering to a living animal in need thereof an effective amount of a compound as defined in claim 1.

4. A method for the treatment of anxiety, depression, disturbances of sleep, vascular, cardiovascular and cerebrovascular disorders, and for the regularization of food consumption and gastric secretion, the step of administering to a living animal in need of the same an effective amount of a compound as defined in claim 1.

5. Method of claim 4 wherein the compound is a compound of claim 2.

6. A pharmaceutical composition useful as an agonist of $5HT_{1A}$ receptors characterized by the fact that it contains an effective amount of a compound of claim 1 in combination with a pharmacologically-acceptable excipient.

7. Composition of claim 6 wherein the compound is a compound of claim 2.

8. A pharmaceutical composition of claim 6 containing also another pharmacologically-active principle.

9. Composition of claim 6 wherein the compound is a compound of claim 2 containing also another pharmacologically-active principle.

10. A process of preparing a chemical compound according to claim 1, characterized by the fact that a compound of formula I is obtained by reaction of a 6-bromo-3,5-dioxo-(2H,4H)-1,2,4-triazine IV with an amine of formula V

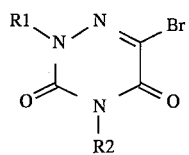

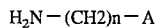

wherein $R_1$ and $R_2$, n, and A have the same meanings as given in claim 1.

11. A process of preparing a chemical compound according to claim 10, characterized by the fact that the reaction between compounds IV and V is carried out under reflux of butanol in the presence of a base.

12. Process of claim 11, wherein the base is triethylamine.

* * * * *

UNITED STATES PATENT AND TRADEMARK OFFICE
CERTIFICATE OF CORRECTION

PATENT NO. : 5,591,743
DATED : January 7, 1997
INVENTOR(S) : J.F. Patoiseaul, F. Couret, C. Faure, E. Dupont-Passelaigue, W. Koek It is certified that error appears in the above-indentified patent and that said Letters Patent is hereby corrected as shown below:

Column 3, line 59: "taken up to" should read -- taken up in --.

Column 4, line 51: Insert a -- - -- (dash) at end of the line after "amino)". Page 9, line 20

Column 4, line 52: Delete the "-" at the beginning of the line.

Column 5, line 5: Insert a -- - -- (dash) at the end of the line after "pyrimidyl)". Page 10, line 11

Column 10, line 50: "(10-5M)," should read -- ($10^{-5}M$), --. Page 22, line 29

Column 13, line 25: Delete the excessive space after "(2H,4H)" and before "-6-(2- ...".

Signed and Sealed this

Twenty-fifth Day of March, 1997

Attest:

BRUCE LEHMAN

Attesting Officer  Commissioner of Patents and Trademarks